US009632981B2

(12) United States Patent
Chan et al.

(10) Patent No.: US 9,632,981 B2
(45) Date of Patent: Apr. 25, 2017

(54) CALIBRATION OF A CHEST-MOUNTED WIRELESS SENSOR DEVICE FOR POSTURE AND ACTIVITY DETECTION

(71) Applicant: Vital Connect, Inc., Campbell, CA (US)

(72) Inventors: Alexander Chan, Campbell, CA (US); Nima Ferdosi, San Jose, CA (US); Ravi Narasimhan, Sunnyvale, CA (US)

(73) Assignee: VITAL CONNECT, INC., San Jose, CA (US)

( * ) Notice: Subject to any disclaimer, the term of this patent is extended or adjusted under 35 U.S.C. 154(b) by 691 days.

(21) Appl. No.: 13/900,438

(22) Filed: May 22, 2013

(65) Prior Publication Data

US 2014/0019080 A1 Jan. 16, 2014

Related U.S. Application Data

(63) Continuation-in-part of application No. 13/548,059, filed on Jul. 12, 2012, now Pat. No. 9,035,794.

(51) Int. Cl.
| | |
|---|---|
| *G01P 21/00* | (2006.01) |
| *G06F 17/00* | (2006.01) |
| *G04F 13/04* | (2006.01) |
| *G07C 1/00* | (2006.01) |
| *A61B 5/00* | (2006.01) |
| *A61B 5/11* | (2006.01) |
| *G01D 21/00* | (2006.01) |
| *G01P 15/00* | (2006.01) |
| *G06F 17/40* | (2006.01) |
| *G06F 19/00* | (2011.01) |

(52) U.S. Cl.
CPC .............. *G06F 17/00* (2013.01); *G01P 21/00* (2013.01); *G04F 13/04* (2013.01); *G07C 1/00* (2013.01); *A61B 5/00* (2013.01); *A61B 5/11* (2013.01); *G01D 21/00* (2013.01); *G01P 15/00* (2013.01); *G06F 17/40* (2013.01); *G06F 19/00* (2013.01)

(58) Field of Classification Search
CPC ........................................................ G01P 21/00
USPC ............................................................ 702/85
See application file for complete search history.

(56) References Cited

U.S. PATENT DOCUMENTS

| | | |
|---|---|---|
| 6,044,297 A | 3/2000 | Sheldon et al. |
| 2007/0115277 A1 | 5/2007 | Wang et al. |
| | (Continued) | |

OTHER PUBLICATIONS

PCT International Search Report and Written Opinion of the International Searching Authority, issued Dec. 2, 2013, application No. PCT/US2013/045321.

*Primary Examiner* — Bryan Bui
(74) *Attorney, Agent, or Firm* — Brundidge & Stanger, P.C.

(57) ABSTRACT

A method and system for calibrating a wireless sensor device are disclosed. In a first aspect, the method comprises determining a vertical calibration vector and determining a rotation matrix using the vertical calibration vector to line up native axes of the wireless sensor device with body axes. In a second aspect, a wireless sensor device comprises a processor and a memory device coupled to the processor, wherein the memory device includes an application that, when executed by the processor, causes the processor to determine a vertical calibration vector and to determine a rotation matrix using the vertical calibration vector to line up native axes of the wireless sensor device with body axes.

18 Claims, 12 Drawing Sheets

(56) References Cited

U.S. PATENT DOCUMENTS

| | | |
|---|---|---|
| 2010/0010583 A1 | 1/2010 | Panken et al. |
| 2010/0298655 A1 | 11/2010 | McCombie et al. |
| 2011/0172927 A1 | 7/2011 | Sahasrabudhe et al. |
| 2011/0201969 A1 | 8/2011 | Hatlestad et al. |
| 2011/0241656 A1 | 10/2011 | Piemonte et al. |
| 2012/0101411 A1 | 4/2012 | Hausdorff et al. |
| 2012/0203487 A1* | 8/2012 | Johnson ................. G01P 21/00 702/104 |
| 2013/0090881 A1* | 4/2013 | Janardhanan ........ G01C 22/006 702/104 |
| 2013/0274830 A1 | 10/2013 | Skelton |

* cited by examiner

CALIBRATION OF A CHEST-MOUNTED WIRELESS SENSOR DEVICE FOR POSTURE AND ACTIVITY DETECTION

CROSS-REFERENCE TO RELATED APPLICATION

This application is a continuation-in-part and claims the benefit of U.S. patent application Ser. No. 13/548,059, filed Jul. 12, 2012, entitled "POSTURE CALIBRATION FOR ACTIVITY MONITORING," which is incorporated herein by reference in its entirety.

FIELD OF THE INVENTION

The present invention relates to wireless sensor devices, and more particularly, to calibration of a chest-mounted wireless sensor device for posture and activity detection.

BACKGROUND

Wireless sensor devices are used in a variety of applications including the posture detection and activity monitoring of users. In many of these applications, a wireless sensor device is attached directly to the user's skin (e.g. near the chest area) to measure certain data. This measured data is then utilized for the posture detection and activity monitoring of the users.

Detecting posture from a patch form-factor chest-mounted wireless sensor device (e.g. accelerometer) is difficult if proper calibration is not performed. This is due to the fact that the patch can be worn in different positions making it difficult to distinguish postures if only non-calibrated accelerometer data is available. Therefore, there is a strong need for a cost-effective solution that overcomes the aforementioned issues. The present invention addresses such a need.

SUMMARY OF THE INVENTION

A method and system for calibrating a wireless sensor device are disclosed. In a first aspect, the method comprises determining a vertical calibration vector and determining a rotation matrix using the vertical calibration vector to line up native axes of the wireless sensor device with body axes.

In a second aspect, a wireless sensor device comprises a processor and a memory device coupled to the processor, wherein the memory device includes an application that, when executed by the processor, causes the processor to determine a vertical calibration vector and to determine a rotation matrix using the vertical calibration vector to line up native axes of the wireless sensor device with body axes.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

Figure 1:
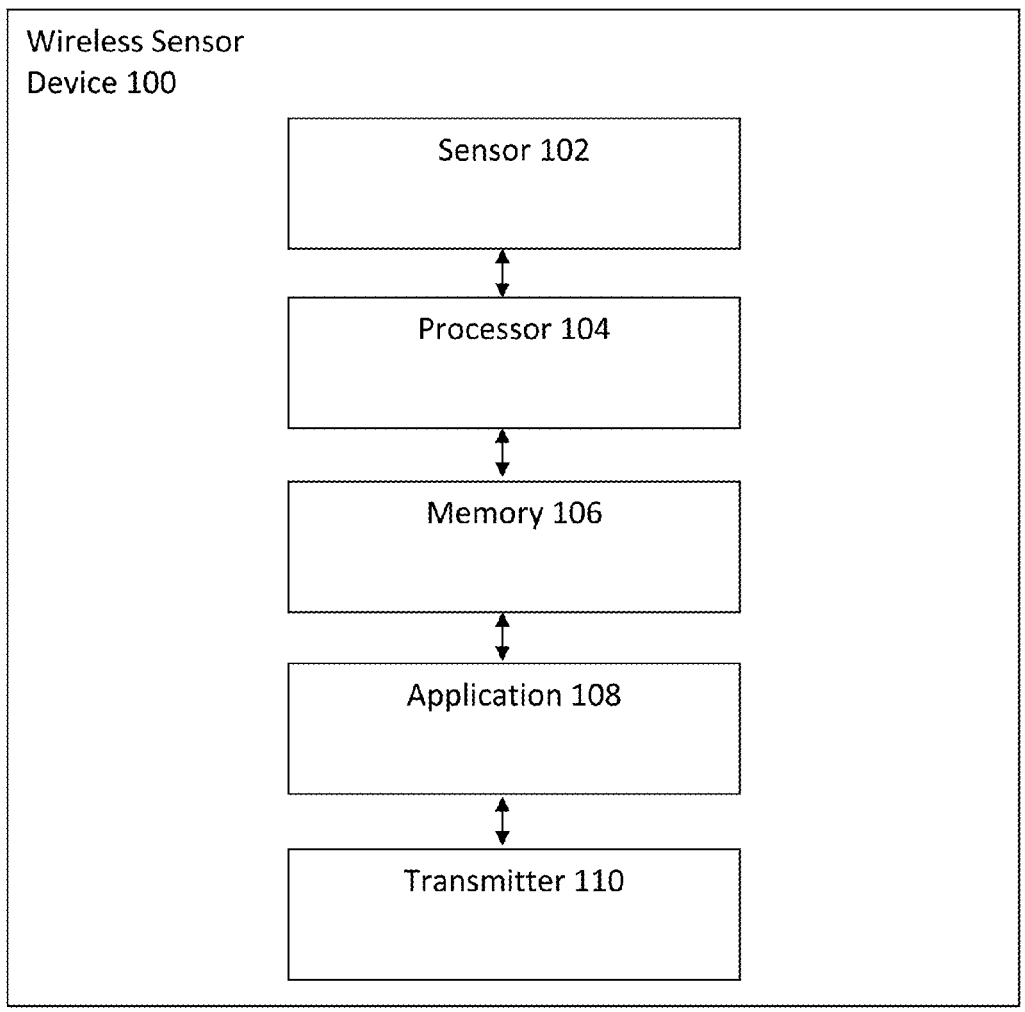
FIG. 1 illustrates a wireless sensor device in accordance with an embodiment.

The present invention relates to wireless sensor devices, and more particularly, to calibration of a chest-mounted wireless sensor device for posture and activity detection. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A wireless sensor device that only utilizes non-calibrated accelerometer data leads to less accurate posture detection and activity level monitoring. Non-calibrated accelerometer data can be arbitrarily positioned relative to the actual body axes. Therefore, a calibration procedure of the wireless sensor device enables the generation of three derived axes of acceleration data that line up with actual body axes: anterior-posterior AP (front-to-back)—Z-axis; medial-lateral ML (left-to-right)—X-axis; and vertical VT (head-to-toe)—Y-axis. The calibration procedure requires determining at least the direction of the VT axis before the VT axis is then used to determine the other 2 axes. In another embodiment, additional calibration during leaning forward or lying supine is utilized to improve calibration accuracy.

A method and system in accordance with the present invention calibrates a wireless sensor device via automatic calibration, manual calibration, and sleep study calibration. In automatic calibration, an algorithm analyzes whether the user is walking and then obtains a vertical calibration vector during this detected walking period. In manual calibration, there is a wireless communication between the patch form-factor wireless sensor device and a relay (e.g. smartphone, handheld device, computer, communication device) that manually calibrates the wireless sensor device when selected or when automatic calibration fails. Manual calibration includes but is not limited to single upright calibration, walking calibration, upright and leaning forward calibration for improved accuracy, and supine and sitting up calibration for bedridden patients. In sleep study calibration, if only sleep data when the user is lying down is available (e.g.

during a sleep study), an algorithm automatically calibrates the wireless sensor device given a whole night of data.

The calibration utilized by the method and system in accordance with the present invention determines a vertical axis VT and uses the VT to determine the other 2 axes. If manual calibration is selected, all of the microelectromechanical systems (MEMS) based algorithms of the wireless sensor device utilize the manual calibration to detect posture and activity levels of the user. If automatic calibration is selected, all of the MEMS based algorithms of the wireless sensor device utilize the automatic calibration to detect posture and activity levels of the user. If neither manual calibration nor automatic calibration is selected, posture detection is disabled and all of the MEMS based algorithms of the wireless sensor device operate in non-calibrated mode.

Once automatic calibration of the wireless sensor device is achieved, the derived calibration vector enables the wireless sensor device to utilize various algorithms that measure the user's activity levels including but not limited to pedometer activity, fall detection, and posture detection. In one embodiment, after attaching the wireless sensor device to the user, the wireless sensor device continuously and automatically obtains varying types of data including but not limited to acceleration samples along an anteroposterior axis of the user. An application embedded within a processor of the wireless sensor device compares the acceleration samples to a threshold to measure the user's activity levels.

One of ordinary skill in the art readily recognizes that a variety of wireless sensor devices can be utilized including but not limited to a wireless sensor device in a patch form-factor, tri-axial accelerometers, uni-axial accelerometers, bi-axial accelerometers, gyroscopes, and pressure sensors and that would be within the spirit and scope of the present invention.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. In one embodiment, the wireless sensor device 100 is attached, in any orientation to a user and on any location of the user. In another embodiment, the wireless sensor device 100 is chest-mounted to the user. The sensor 102 obtains data from the user and transmits the data to the memory 106 and in turn to the application 108. The processor 104 executes the application 108 to monitor information regarding the user's posture and activity levels. The information is transmitted to the transmitter 110 and in turn relayed to another user or device.

In one embodiment, the sensor 102 is a microelectromechanical system (MEMS) tri-axial accelerometer and the processor 104 is a microprocessor. One of ordinary skill in the art readily recognizes that a variety of devices can be utilized for the processor 104, the memory 106, the application 108, and the transmitter 110 and that would be within the spirit and scope of the present invention.

To describe the features of the present invention in more detail, refer now to the following description in conjunction with the accompanying Figures.

Automatic Calibration:

The wireless sensor device can be automatically calibrated utilizing an acceleration vector corresponding to the footsteps of the user while walking. Automatic calibration starts after the wireless sensor device is powered on and is attached to the body of the user (typically the chest area). During a predetermined time period (e.g. the first fifteen minutes) after the attachment of the wireless sensor device, an acceleration vector corresponding to the footsteps of the user is detected and is utilized to calculate a calibration vector. If during the predetermined time period, at least a predetermined number of steps (e.g. 25 steps) by the user are not detected, the automatic calibration process is terminated and the MEMS based algorithms of the wireless sensor device operate in the non-calibrated mode.

In one embodiment, the automatic calibration process is repeated every time the wireless sensor device patch is applied to the skin of the user to ensure correct calibration in use-cases when the user changes position of the patch without power-cycling it. In another embodiment, the automatic calibration process and resulting calibration vector is given less priority than any form of manual calibration and the calibration vector derived from any form of manual calibration overrides the calibration vector derived from automatic calibration.

In order to accurately detect when the user is walking for the automatic calibration, a walking detection algorithm that does not depend on the calibration is utilized by the wireless sensor device to determine when the user is walking for the step count. In one embodiment, the walking detection algorithm comprises: retrieving a predetermined time period window (e.g. 1 second) of raw accelerometer data in the 3 axes (x, y, z), computing the signal magnitude area (SMA) for the predetermined time period window, computing the magnitude of acceleration in the horizontal plane ($mag_{horz}$) and overall ($mag_{total}$), and comparing the calculated SMA and magnitude of accelerations to various thresholds.

Figure 2:
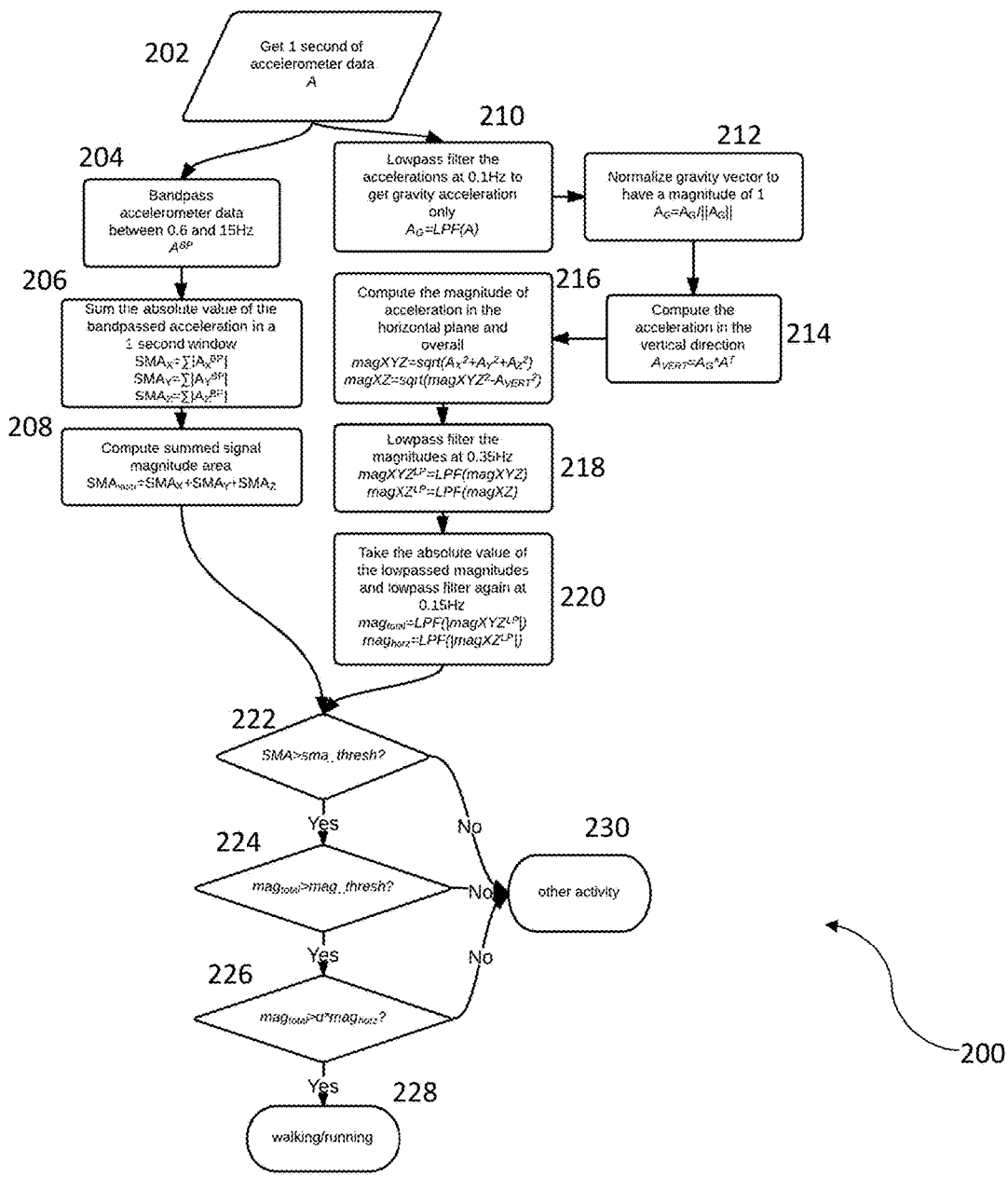
FIG. 2 illustrates a method of a wireless sensor device utilizing a walking detection algorithm in accordance with an embodiment.

FIG. 2 illustrates a method 200 for a wireless sensor device utilizing a walking detection algorithm in accordance with an embodiment. In the method 200, the wireless sensor device retrieves 1 second of raw accelerometer data in the 3 axes (x, y, z), via step 202. To calculate the signal magnitude area (SMA) for the 1 second window, the wireless sensor device bandpass filters a signal, detected by the wireless sensor device, between 0.6 Hz and 15 Hz to derive $A^{BP}$, via step 204, sums an absolute value of the filtered signal for the 1 second window where $SMA_X=\Sigma|A_X^{BP}|$, $SMA_Y=\Sigma|A_Y^{BP}|$, $SMA_Z=\Sigma|A_Z^{BP}|$, via step 206, and sums the results for each of the 3 axes to get an overall $SMA_{sum}$ value where $SMA_{sum}=SMA_X+SMA_Y+SMA_Z$, via step 208.

To calculate the magnitude of acceleration in the horizontal plane ($mag_{horz}$) and overall ($mag_{total}$), the wireless sensor device lowpass filters the raw acceleration at 0.1 Hz to derive a gravity component $A_G$ where $A_G=LPF(A)$, via step 210, normalizes the gravity component to derive a magnitude of 1, where $A_G=A_G/\|A_G\|$, via step 212, calculates an acceleration in a vertical direction $A_{VERT}$, where $A_{VERT}=A_G*A^T$, via step 214, calculates an overall magnitude of acceleration as $magXYZ=sqrt(A_X^2 \pm A_Y^2 + A_Z^2)$ and a magnitude of acceleration in the horizontal plane as $magXZ=sqrt(magXYZ^2-A_{VERT}^2)$, via step 216, lowpass filters the magnitudes derived in step 216 at 0.35 Hz to derive $magXYZ^{LP}$ and $magXZ^{LP}$, via step 218, and takes an absolute value of the lowpass magnitudes derived in step 218 and lowpass filter again at 0.15 Hz to derive $mag_{total}=LPF(|magXYZ^{LP}|)$ and $mag_{horz}=LPF(|magXZ^{LP}|)$, via step 220.

After computing the SMA and the magnitude of acceleration in both the horizontal plane and overall, the wireless sensor device analyzes whether SMA is greater than a threshold sma_thresh, via step 222. If yes (SMA>sma_thresh), the wireless sensor device analyzes whether $mag_{total}$ is greater than a threshold mag_thresh, via step 224. If yes (mag$_{total}$>mag_thresh), the wireless sensor device analyzes whether mag$_{total}$ is greater than the mag$_{horz}$ times a constant α (e.g. α=1), via step 226. If yes (mag$_{total}$>α·mag$_{horz}$), then the wireless sensor device classifies the current time and activity as walking, via step 228. If any of steps 222-226 are not met, then the wireless sensor device classifies the current time and activity as another activity, via step 230.

Figure 3:
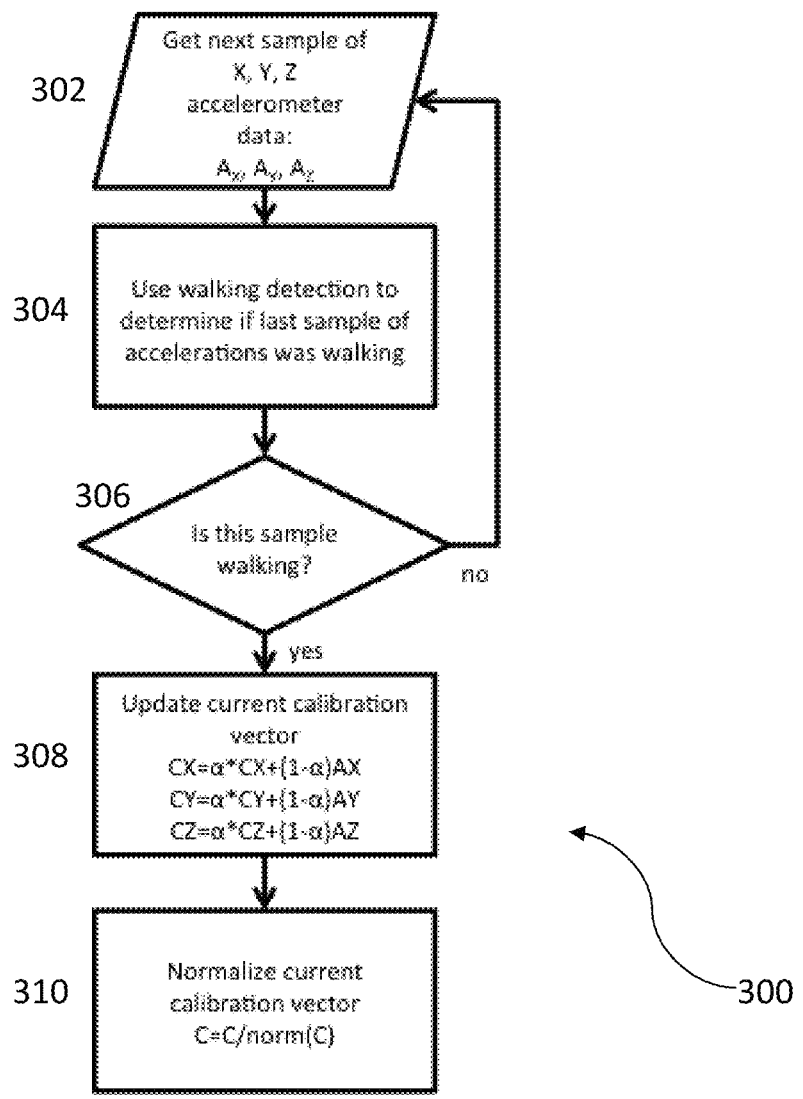
FIG. 3 illustrates a method for adaptive calibration in accordance with an embodiment.

Adaptive Calibration:

Occasionally, the implicit/automatic calibration based on walking is inaccurate and confuses another activity for walking. In this case, the wireless sensor device 100 utilizes adaptive calibration to correct for incorrect calibrations over time. The wireless sensor device 100 analyzes periods of walking and slowly adjusts the calibration vector over time. The calibration vector is adjusted by adding a small amount of the current acceleration during walking and renormalizing each time. FIG. 3 illustrates a method 300 for adaptive calibration in accordance with an embodiment.

In the method 300, a wireless sensor device retrieves a next sample of x, y, z accelerometer data (A$_X$, A$_Y$, A$_Z$), via step 302, and utilizes walking detection to determine if a last sample of accelerometer data/accelerations was walking, via step 304. If the wireless sensor device determines that the last sample is of walking, via step 306, the current calibration vector is updated per CX=α*CX+(1−α)A$_X$, CY=α*CY+(1−α)A$_Y$, CZ=α*CZ+(1−α)A$_Z$, via step 308. To complete the adaptive calibration, the wireless sensor device normalizes the current calibration vector per C=C/norm(C), via step 310.

In the adaptive calibration, α is a parameter that determines how slowly the calibration vector is adjusted (e.g. the closer to 1, the slower the adaptation). In one embodiment, the value of α=0.999973 resulting in a time-constant of 10 minutes for a sampling rate of 62.5 Hz.

Manual Calibration:

The wireless sensor device can also be manually/explicitly calibrated utilizing a variety of methodologies including but not limited to a manual calibration based on the user's upright position, a manual calibration based on walking/taking steps, and a manual calibration based on a bedridden user. During explicit calibration, the user, through an interface like a relay (e.g. smartphone) or through a predefined protocol (e.g. standing upright at the time of attaching the patch form-factor wireless sensor device to the user), informs the wireless sensor device of his/her posture.

The calibration vector acquired through the latest manual calibration will override the calibration vector derived from automatic calibration and earlier manual calibrations of the same type. Manual calibration requires an interaction between the user and the relay as well as the relay and the wireless sensor device. Bedridden users incapable of standing upright will go through two steps of calibration based on leaning-back and lying down flat in supine postures.

Figure 4:
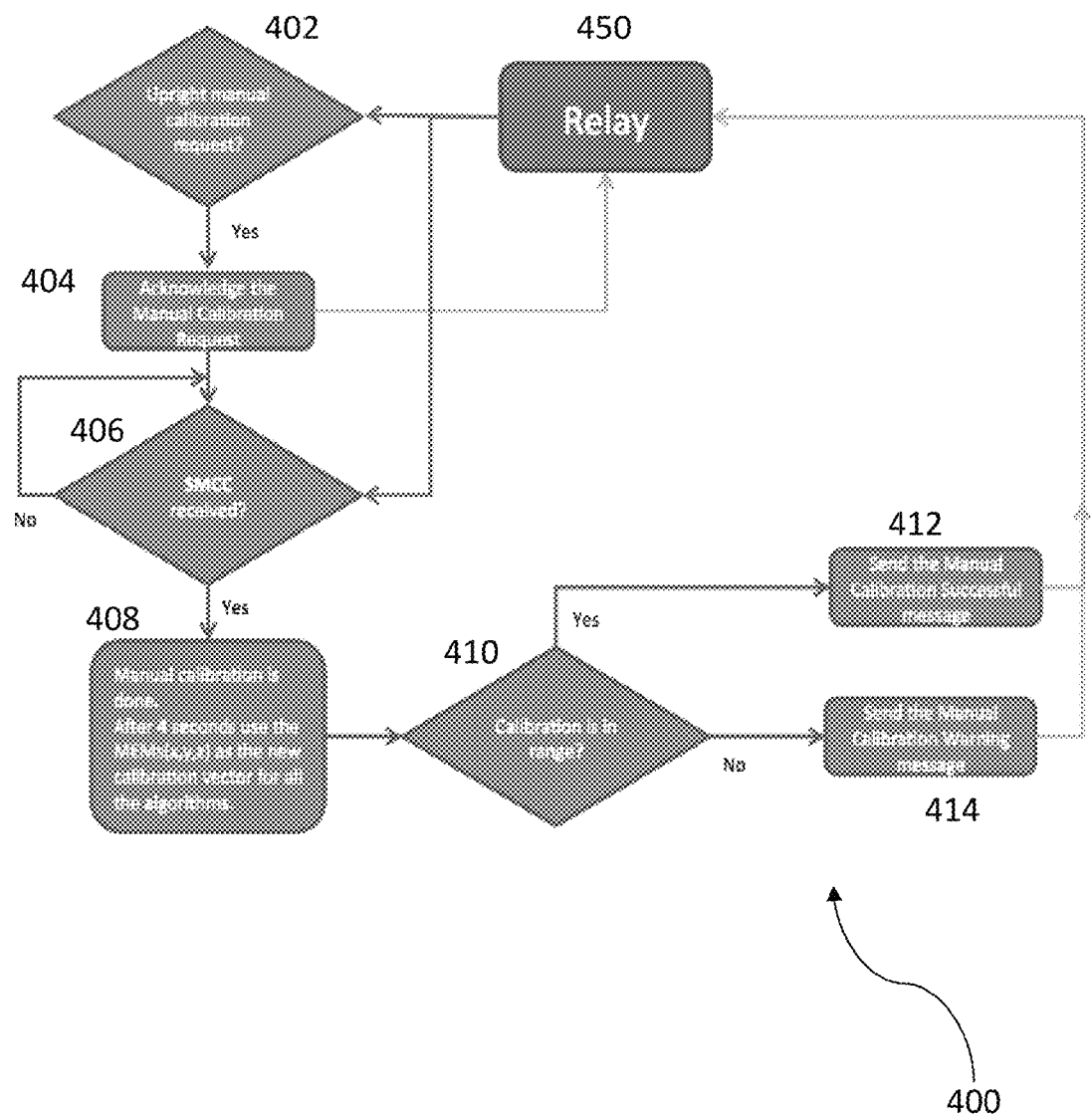
FIG. 4 illustrates a method for upright manual calibration in accordance with an embodiment.

FIG. 4 illustrates a method 400 for upright manual calibration in accordance with an embodiment. In the method 400, a wireless sensor device receives a Manual Calibration Request from the user based upon a standing upright position, via step 402, and acknowledges the receipt of the Manual Calibration Request, via step 404. After receiving the Manual Calibration Request from the user, the wireless sensor device waits for a predetermined time period (e.g. 4 seconds) to receive a Start Manual Calibration Command (SMCC) from a relay 450, via step 406.

In one embodiment, the relay 450 is a communication device including but not limited to a smartphone, handheld device, and a computer. After receiving the Start Manual Calibration Command, the wireless sensor device determines a New Upright Calibration Vector and waits for another predetermined time period (e.g. 4 seconds) before replacing the Current Upright Calibration Vector with the New Upright Calibration Vector that is a lowpass filtered MEMS vector (x, y, z), via step 408.

The calibration is within range if the angle of the New Upright Calibration Vector versus the vertical axis of the wireless sensor device is less than 30 degrees. The wireless sensor device determines whether the calibration is within range, via step 410. If yes (the calibration is within range), then the wireless sensor device transmits a Manual Calibration Success status to the relay 450, via step 412. If no (the calibration is not within range), then the wireless sensor device transmits a Manual Calibration Warning status to the relay 450, via step 414.

In one embodiment, after the upright calibration is performed, an additional calibration is performed on the wireless sensor device to improve the accuracy of the calibration. In the additional calibration, the user is instructed to bend over and remain in this position for a predetermined time period (e.g. 5 seconds) to provide a second calibration vector which improves the overall calibration. The second calibration vector allows for an exact determination of the medial-lateral (ML) and anteroposterior (AP) axes, as opposed to an estimate if provided with only a single upright calibration.

Figure 5:
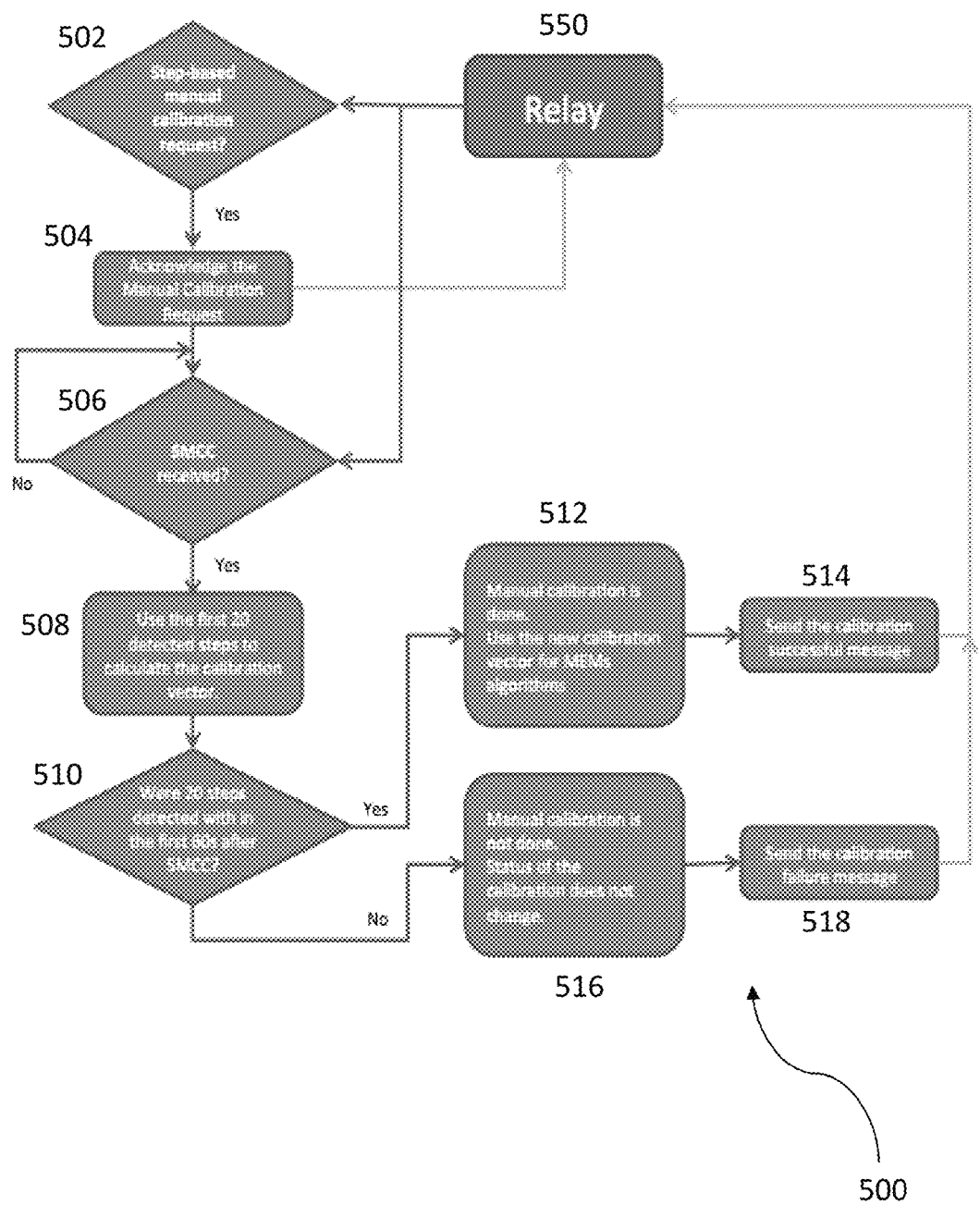
FIG. 5 illustrates a method for manual calibration based on walking in accordance with an embodiment.

FIG. 5 illustrates a method 500 for manual calibration based on walking in accordance with an embodiment. In the method 500, a wireless sensor device receives a Manual Calibration Request from the user based on walking/taking steps, via step 502, and acknowledges the receipt of the Manual Calibration Request, via step 504. After receiving the Manual Calibration Request from the user, the wireless sensor device waits for a predetermined time period (e.g. 4 seconds) to receive a Start Manual Calibration Command (SMCC) from a relay 550, via step 506.

In one embodiment, the relay 550 is a communication device including but not limited to a smartphone, handheld device, and a computer. After receiving the Start Manual Calibration Command, the wireless sensor device utilizes the first predetermined number of steps (e.g. the first 20 steps) to calculate a New Upright Calibration Vector, via step 508.

The wireless sensor device determines whether the predetermined number of steps have been detected within a predetermined time period (e.g. 60 seconds) after receiving the SMCC (the start of the calibration), via step 510. If yes, the manual calibration is completed and the wireless sensor device replaces the Current Upright Calibration Vector with the New Upright Calibration Vector for utilization by the MEMS algorithms, via step 512. If no, the manual calibration is not completed and the status of the calibration does not change and the Current Upright Calibration Vector is maintained and not replaced by the New Upright Calibration Vector which is instead discarded, via step 516.

The wireless sensor device also determines whether the calibration is within range. The calibration is within range if the angle of the New Upright Calibration Vector versus the vertical axis of the wireless sensor device is less than 30 degrees. Based upon step 510 and the determination of whether the calibration is within range, the wireless sensor device transmits a manual calibration status message to the relay 550.

A Manual Calibration Success status is transmitted to the relay 550, via step 514, if at least the predetermined number of steps is detected within the predetermined time period after the start of the calibration per step 510 and the calibration is within range. A Manual Calibration Warning status is transmitted to the relay 550 if at least the predetermined number of steps is detected within the predetermined time period after the start of the calibration per step 510 but the calibration is not within range.

In the cases of a "success" and "warning" message, the wireless sensor device updates the calibration vector with the New Upright Calibration Vector that replaces the Current Upright Calibration Vector. A Manual Calibration Failure status is transmitted to the relay 550, via step 518, if at least the predetermined number of steps is not detected within the predetermined time period after the start of the calibration per step 510. In the case of a "failure" message, the wireless sensor device does not update the calibration vector and so the Current Upright Calibration Vector is not replaced.

Figure 6:
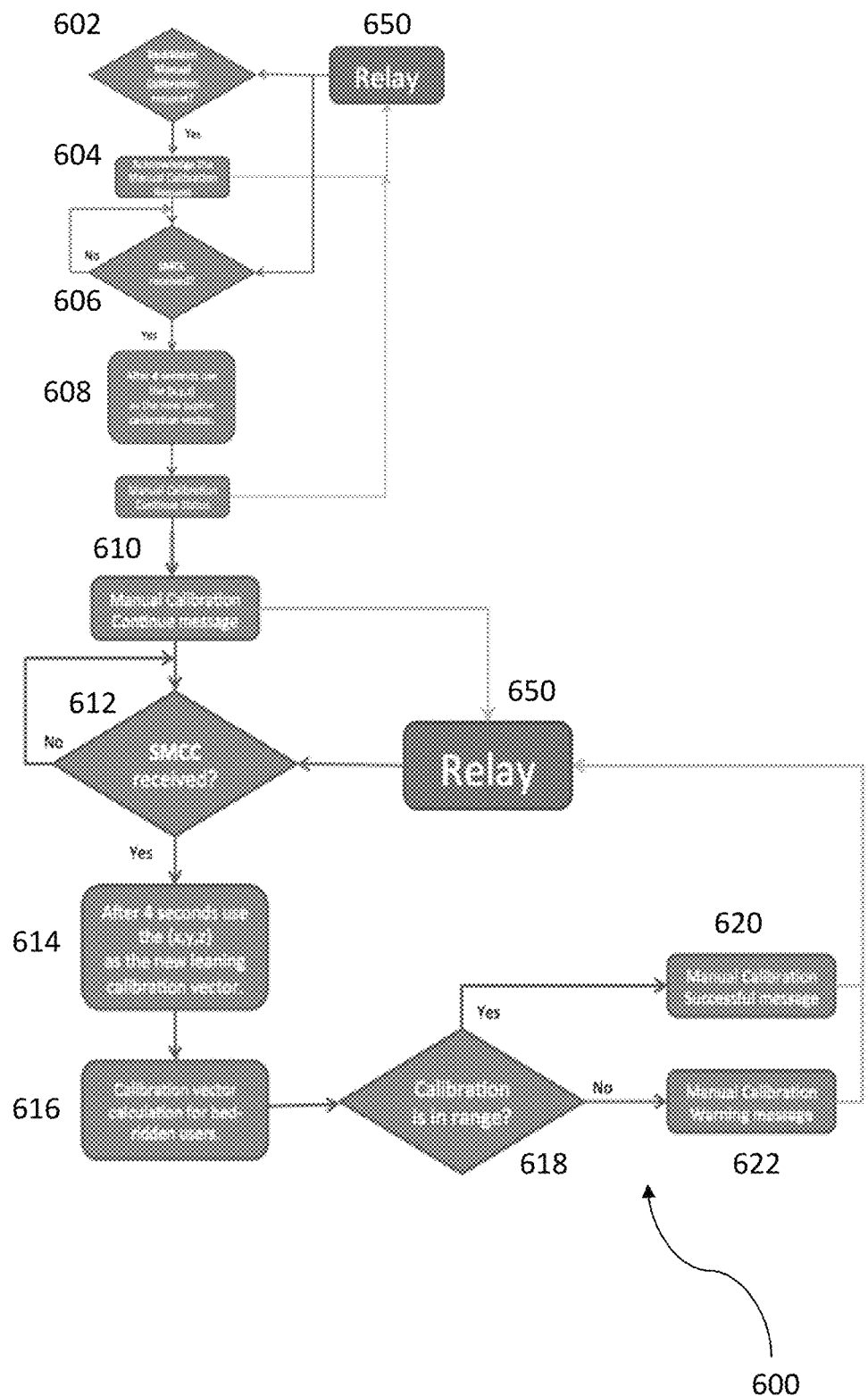
FIG. 6 illustrates a method for manual calibration of a bedridden user in accordance with an embodiment.

FIG. 6 illustrates a method 600 for manual calibration of a bedridden user in accordance with an embodiment. In the method 600, a wireless sensor device receives a Manual Calibration Request from the bedridden user or another user (e.g. nurse, assistant), via step 602, and acknowledges the receipt of the Manual Calibration Request, via step 604. After receiving the Manual Calibration Request from the user, the wireless sensor device waits for a first predetermined time period (e.g. 4 seconds) to receive a first Start Manual Calibration Command (SMCC) from a relay 650, via step 606.

In one embodiment, the relay 650 is a communication device including but not limited to a smartphone, handheld device, and a computer. After receiving the first Start Manual Calibration Command, the wireless sensor device waits for a second predetermined time period (e.g. 4 seconds) before replacing the Current Supine Calibration Vector with a New Supine Calibration Vector that is a lowpass filtered MEMS vector (x, y, z) determined while the user is flat on his/her back, via step 608.

The wireless sensor device sends a Manual Calibration Continue status message to the relay 650, via step 610, and waits for a third predetermined time period (e.g. 4 seconds) to receive a second Start Manual Calibration Command (SMCC) from the relay 650, via step 612. After receiving the second Start Manual Calibration Command, the wireless sensor device waits for a fourth predetermined time period (e.g. 4 seconds) before replacing the Current Leaning Calibration Vector with a New Leaning Calibration Vector that is a lowpass filtered MEMS vector (x, y, z) determined while the user is in a slightly raised position on his/her back, via step 614.

The wireless sensor device calculates the calibration vector for the bedridden user, via step 616, and then determines whether the calibration based on both leaning back and supine calibrations is within range, via step 618. The calibration is within range if the angle of the New Leaning Calibration Vector versus the vertical axis of the wireless sensor device is less than 30 degrees and if the angle of the New Supine Calibration Vector versus the vertical axis of the wireless sensor device is less than 30 degrees. If yes (calibration is within range), the wireless sensor device sends a Manual Calibration Success status message to the relay 650, via step 620, and if no (calibration is not within range), the wireless sensor device sends a Manual Calibration Warning status message to the relay 650, via step 622.

Therefore, the types of Manual Calibration Requests inputted via a relay or smartphone application by the user of the wireless sensor device include but are not limited to an upright manual calibration request, a walking manual calibration request, and a bedridden user manual calibration request. After receiving and acknowledging one of these types of requests, the wireless sensor device waits to receive the SMCC once the user has received various instructions and is ready for the calibration to begin (e.g. is in the correct position). After receiving the SMCC, the wireless sensor device performs the requested method of calibration and sends the manual calibration status messages to the relay which informs the user of the status message.

The New Upright Calibration Vector determined from FIGS. 4 and 5 represents the vertical calibration vector utilized to generate a rotation matrix. In the case of a bedridden subject, the New Leaning Calibration Vector and the New Supine Calibration Vector determined from FIG. 6 are used to generate a vertical calibration vector and a leaning calibration vector that are both utilized to generate a rotation matrix. Once the vertical calibration vector is obtained, the native axes, or the uncalibrated MEMS axes, of the wireless sensor device with embedded accelerometer are rotated to line up with the user's body axes. The rotation matrix is generated with a single upright calibration vector or with the combination of an upright calibration vector and a leaning (forward or backwards) calibration vector.

For the rotation matrix calculation notation, $X_{i,f}$ equals a vector $X_i$ in the frame of reference f, $R_{n,m}$ is the rotation matrix converting from frame of reference n to frame of reference m, $X_{i,i}$, $Y_{i,i}$, and $Z_{i,i}$ are the basis accelerometer axes in frame i where $X_{i,i}=[1\ 0\ 0]^T$, $Y_{i,i}=[0\ 1\ 0]^T$, $Z_{i,i}=[0\ 0\ 1]^T$, and $C_{VT}$, $C_{lean}$, $C_{SP}$ are the calibration vectors for vertical, leaning, and supine positions respectively. After calculation, the final body axes is represented by X-axis ($X_B$): pointing to the right, Y-axis ($Y_B$): pointing inferiorly (towards feet), and Z-axis ($Z_B$): pointing anteriorly (forward from chest).

Figure 7:
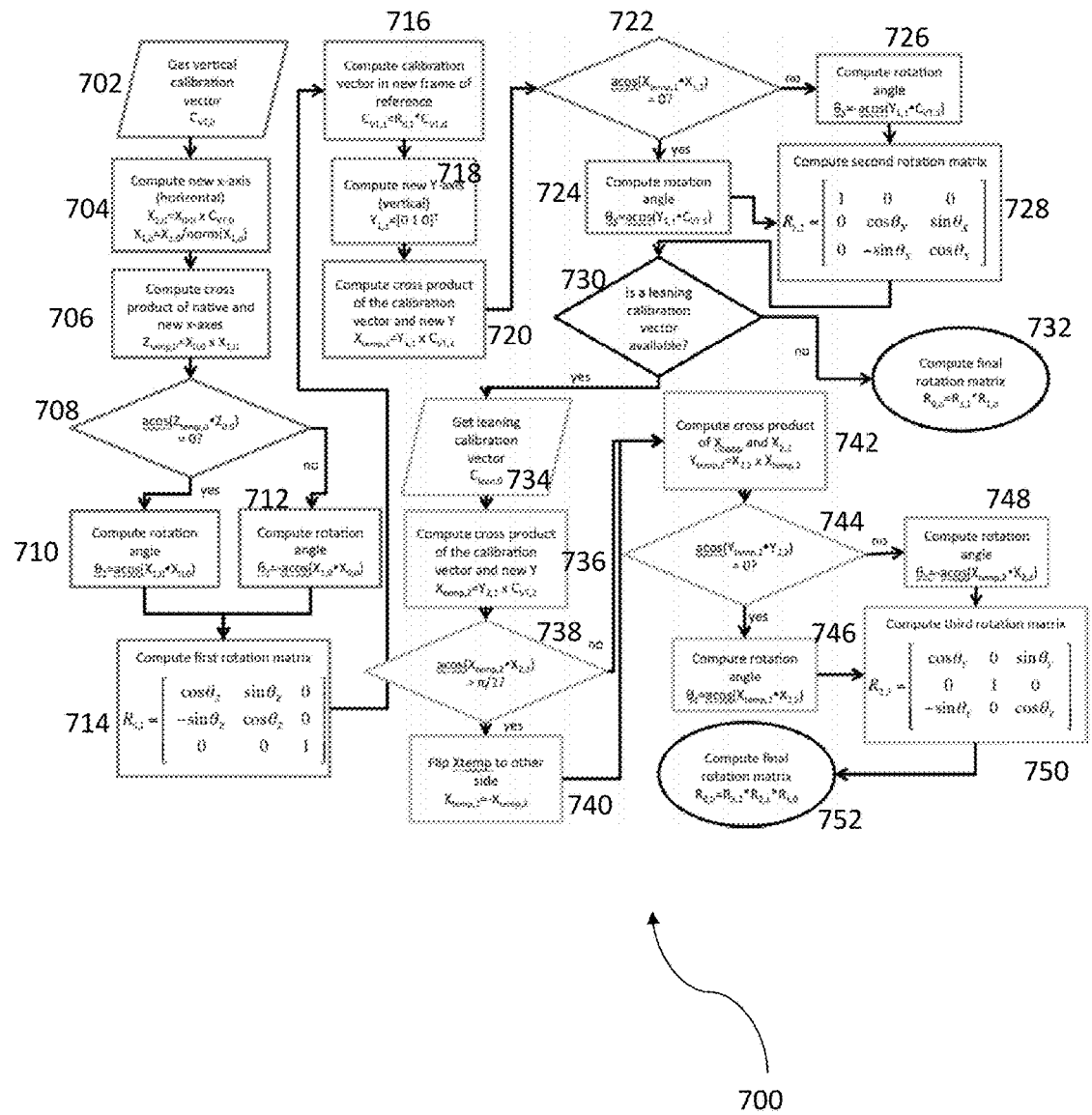
FIG. 7 illustrates a method for calculating a rotation matrix in accordance with an embodiment.

FIG. 7 illustrates a method 700 for calculating a rotation matrix in accordance with an embodiment. In the method 700, steps 702-714 represent a first section of a rotation matrix algorithm that rotates the native wireless sensor device's accelerometer axes to line up the X-axis ($X_{0,0}$) with the horizontal plane (some combination of medial-lateral ML and anterior-posterior AP); steps 716-728 represent a second section of the rotation matrix algorithm that rotates the native accelerometer axes to line up the Y-axis ($Y_{1,1}$) to the body axis VT ($Y_B$); and steps 734-750 represent a third section of the rotation matrix algorithm that rotates the X-axis ($X_{2,2}$) to align with the body axis ML ($X_B$) and that rotates the Z-axis ($Z_{2,2}$) to align with the body axis AP ($Z_B$), if an additional leaning calibration vector is provided.

The first and second sections are carried out by the wireless sensor device as long as a VT calibration vector is initially determined via step 702. The third section requires a leaning calibration vector input to also be provided and results in exact calculations of ML and AP. If the leaning calibration vector input is not provided, the wireless sensor device only determines an approximation of ML and AP because the X-axis and Z-axis are aligned horizontally but not aligned with the actual body axes.

In the method 700, the wireless sensor device determines a vertical calibration vector ($C_{VT,0}$) in accordance with one of the aforementioned manual calibration procedures described by FIG. 4-6, via step 702. The wireless sensor device calculates a new horizontal X-axis ($X_{1,0}$) per the equations $X_{1,0}=X_{0,0}*C_{VT,0}$ and $X_{1,0}=X_{1,0}/\text{norm}(X_{1,0})$, via step 704. The wireless sensor device calculates a cross product ($Z_{temp,0}$) of the native and the new X-axis per the equation $Z_{temp,0}=X_{0,0}\times X_{1,0}$, via step 706, and then determines whether a $\cos(Z_{temp,0}*Z_{0,0})=0$, via step 708.

If yes (a $\cos(Z_{temp,0}*Z_{0,0})=0$), then the wireless sensor device calculates a rotation angle per the equation $\square_Z=a$ $\cos(X_{1,0} \cdot X_{0,0})$, via step 710, and if no (a $\cos(Z_{temp,0}*Z_{0,0})$ does not equal 0), then the wireless sensor device calculates a rotation angle per the equation $\square_Z = -a\cos(X_{1,0} \cdot X_{0,0})$, via step 712.

The wireless sensor device calculates a first rotation matrix ($R_{0,1}$) per the equation $$R_{0,1} = \begin{bmatrix} \cos\theta_z & \sin\theta_z & 0 \\ -\sin\theta_z & \cos\theta_z & 0 \\ 0 & 0 & 1 \end{bmatrix},$$

via step 714, which completes the first section of the rotation matrix algorithm. To begin the second section of the rotation matrix algorithm, the wireless sensor device calculates a calibration vector in a new frame of reference per the equation $C_{VT,1} = R_{0,1}*C_{VT,0}$, via step 716, and calculates a new vertical Y-axis per the equation $Y_{1,1} = [0\ 1\ 0]^T$, via step 718. After these two computations, the wireless sensor device calculates a cross product ($X_{temp,1}$) of the calibration vector $C_{VT,1}$ and the new Y-axis $Y_{1,1}$ per the equation $X_{temp,1} = Y_{1,1} \times C_{VT,1}$, via step 720.

The wireless sensor device determines whether a $\cos(X_{temp,1}*X_{1,1})=0$, via step 722. If yes (a $\cos(X_{temp,1}*X_{1,1})=0$), then the wireless sensor device calculates a rotation angle per the equation $\square_X = a\cos(Y_{1,1} \cdot C_{VT,1})$, via step 724, and if no (a $\cos(X_{temp,1}*X_{1,1})$ does not equal 0), then the wireless sensor device calculates a rotation angle per the equation $\square_X = -a\cos(Y_{1,1} \cdot C_{VT,1})$, via step 726. The wireless sensor device calculates a second rotation matrix ($R_{1,2}$) per the equation $$R_{1,2} = \begin{bmatrix} 1 & 0 & 0 \\ 0 & \cos\theta_X & \sin\theta_X \\ 0 & -\sin\theta_X & \cos\theta_X \end{bmatrix},$$

via step 728, which completes the second section of the rotation matrix algorithm.

The wireless sensor device then determines whether a leaning calibration vector is available, via step 730. If no, the rotation matrix algorithm ends with the wireless sensor device computing a final rotation matrix ($R_{B,0}$) per the equation $R_{B,0} = R_{2,1}*R_{1,0}$, via step 732. If yes (a leaning calibration vector is available for the wireless sensor device to utilize), then the third section of the rotation matrix algorithm is initiated with the wireless sensor device obtaining the leaning calibration vector ($C_{lean,0}$), via step 734.

The wireless sensor device calculates a cross product of the calibration vector and the new Y-axis per the equation $X_{temp,2} = Y_{2,2} \times C_{VT,2}$, via step 736. If a $\cos(X_{temp,2} \cdot X_{2,2})$ is determined to be more than $\pi/2$, via step 738, then the wireless sensor device flips $X_{temp}$ to the other side per the equation $X_{temp,2} = -X_{temp,2}$, via step 740 The wireless sensor device calculates a cross product ($Y_{temp,2}$) of $X_{temp,2}$ and $X_{2,2}$ per the equation $Y_{temp,2} = X_{2,2} \times X_{temp,2}$, via step 742, and determines whether a $\cos(Y_{temp,2} \cdot Y_{2,2})=0$, via step 744. If yes (a $\cos(Y_{temp,2} \cdot Y_{2,2})=0$), then the wireless sensor device calculates a rotation angle per the equation $\square_Y = a\cos(X_{temp,2} \cdot X_{2,2})$, via step 746, and if no (a $\cos(Y_{temp,2} \cdot Y_{2,2})$ does not equal 0), then the wireless sensor device calculates a rotation angle per the equation $\square_Y = -a\cos(X_{temp,2} \cdot X_{2,2})$, via step 748.

After computing the rotation angle, the wireless sensor device calculates a third rotation matrix ($R_{2,3}$) per the equation $$R_{2,3} = \begin{bmatrix} \cos\theta_Y & 0 & \sin\theta_Y \\ 0 & 1 & 0 \\ -\sin\theta_Y & 0 & \cos\theta_Y \end{bmatrix},$$

via step 750, and calculates the final rotation matrix ($R_{B,0}$) per the equation $R_{B,0} = R_{3,2}*R_{2,1}*R_{1,0}$, via step 752 to conclude the rotation matrix algorithm.

In one embodiment, if the calibration vectors determined by or provided to the wireless sensor device are not the upright and leaning calibration vectors, but are instead the supine and leaning calibration vectors, the upright calibration vector (VT) is derived by the wireless sensor device.

In one embodiment, during the calibration for bedridden subjects, the supine and leaning calibration vectors are obtained, but a vertical and leaning vector are required for generating the rotation matrix. The vertical calibration vector VT is derived from the supine and leaning calibration vectors. The wireless sensor device determines the upright calibration vector VT by taking the cross product of the supine ($C_{SP}$) and leaning ($C_{lean}$) calibration vectors to calculate a horizontal vector ($C_{horz}$) per the equation $C_{horz} = C_{lean} \times C_{SP}$, taking the cross product of the horizontal and supine calibration vectors to calculate a vertical calibration vector ($C_{VT}$) per the equation $C_{VT} = C_{SP} \times C_{horz}$. At this point, the rotation matrix algorithm described by FIG. 7 is utilized with $C_{VT}$ as the vertical calibration vector and $C_{SP}$ as the leaning calibration vector.

In one embodiment, the wireless sensor device in a patch form-factor is used only during a sleep study where periods of upright positioning are rare or not captured. In this embodiment, the calibration is achieved via a sleep study algorithm using only sleep data with the assumptions that the user is lying on his/her back for most of the period of data collection, the user is supine for some period of the night, the user is in at least two of the other lying subpostures (left lateral, right lateral, prone) for some period of the night, and the patch is worn on the front of the user's chest.

During periods of inactivity, the wireless sensor device utilizes the sleep study algorithm to determine a gravity vector for every predetermined number of seconds (N). A plane is fit such that all of the gravity vectors lie in the plane and the normalization of the plane is the vertical calibration vector VT. The supine calibration vector position $C_{SP}$ is found utilizing the sleep study algorithm and serves as the leaning calibration vector and a rotation matrix is calculated from these two calibration vectors VT and $C_{SP}$.

Figure 8:
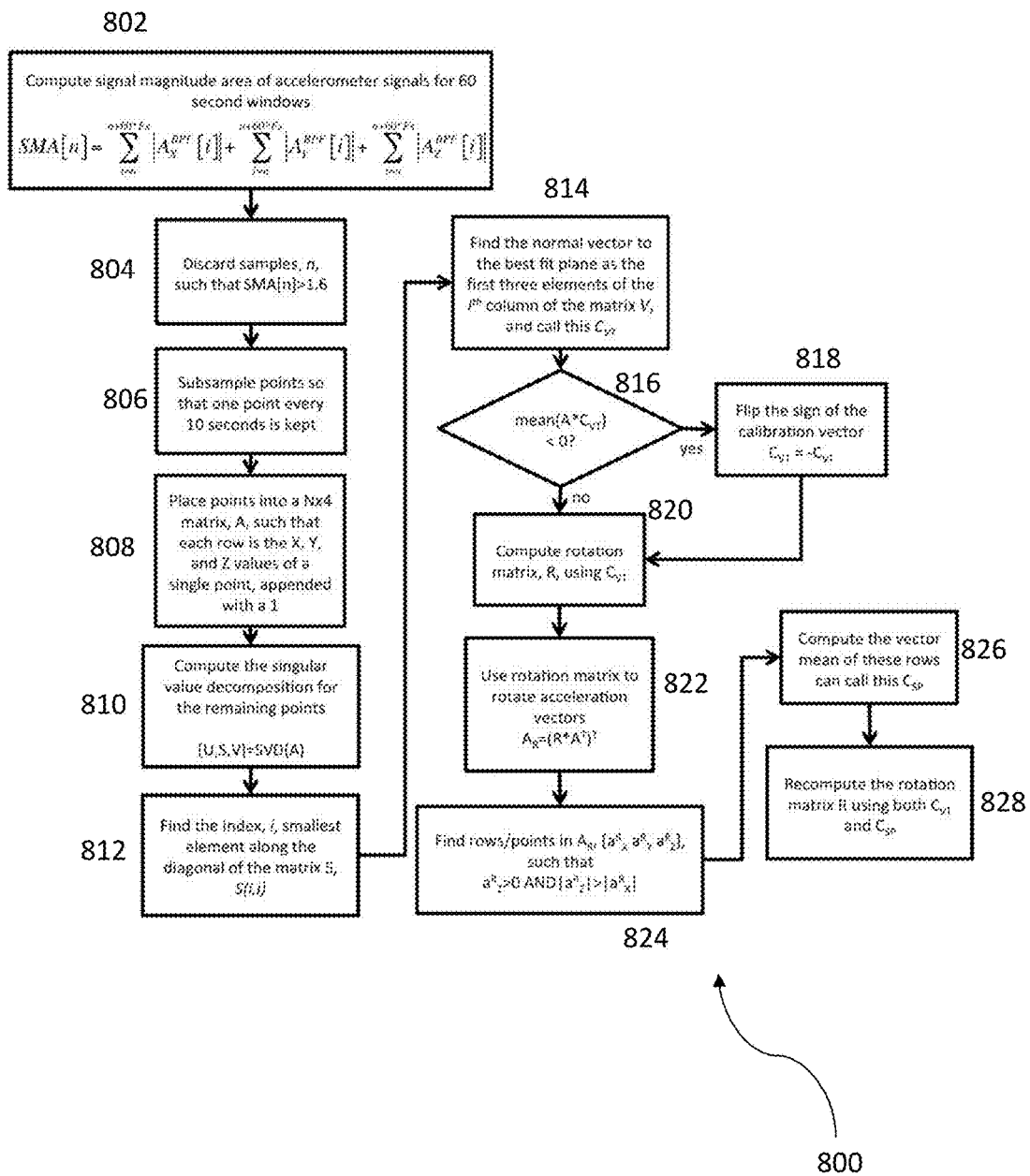
FIG. 8 illustrates a method for calculating a rotation matrix using data from a sleep study in accordance with an embodiment.

FIG. 8 illustrates a method 800 for calculating a rotation matrix using a sleep study algorithm in accordance with an embodiment. In the method 800, a wireless sensor device calculates a signal magnitude area of accelerometer signals for 60 second windows per the equation:

$$SMA[n] = \sum_{i=n}^{n+60*Fs} |A_X^{BPF}[i]| + \sum_{i=n}^{n+60*Fs} |A_Y^{BPF}[i]| + \sum_{i=n}^{n+60*Fs} |A_Z^{BPF}[i]|,$$

via step 802.

The wireless sensor device discards samples, n, such that SMA[n]>1.6, via step 804, and subsamples points so that one point every 10 seconds is kept, via step 806. Using singular value decomposition (SVD), the wireless sensor device calculates a best fit plane and normalizes the vector $C_{VT}$ by placing points into a N×4 matrix, A, such that each row is the X, Y, and Z values of a single point, appended with a 1, via step 808. The SVD is calculated for the remaining points per the equation [U,S,V]=SVD(A), via step 810 and the index, i, is found as the smallest element along the diagonal of the matrix S per S(i,i), via step 812. The wireless sensor device determines a normal vector to the best fit plane as the first three elements of the $i^{th}$ column of the matrix V which represents $C_{VT}$, via step 814.

At this point, it is unknown whether $C_{VT}$ is pointing towards the user's head or feet and so the wireless sensor device determines if a mean of the point projections is positive or negative per the equation mean($A*C_{VT}$)<0, via step 816, and flips the sign if necessary, via step 818. The wireless sensor device calculates a rotation matrix R using $C_{VT}$, via step 820, and uses the rotation matrix to rotate the acceleration vectors per the equation $A_R=(R*A^T)^T$ to find points that correspond to the supine calibration vector, via step 822. The wireless sensor device determines the rows/points in $A_R$, $[a^R_x a^R_y a^R_z]$, such that $a^R_z>0$ and $|a^R_z|>|a^R_x|$, via step 824 and computes the vector mean of these rows to find the supine calibration vector $C_{SP}$, via step 826. To conclude the sleep study algorithm, the rotation matrix R is recalculated by the wireless sensor device using both the newly determined $C_{VT}$ and $C_{SP}$.

Figure 9:
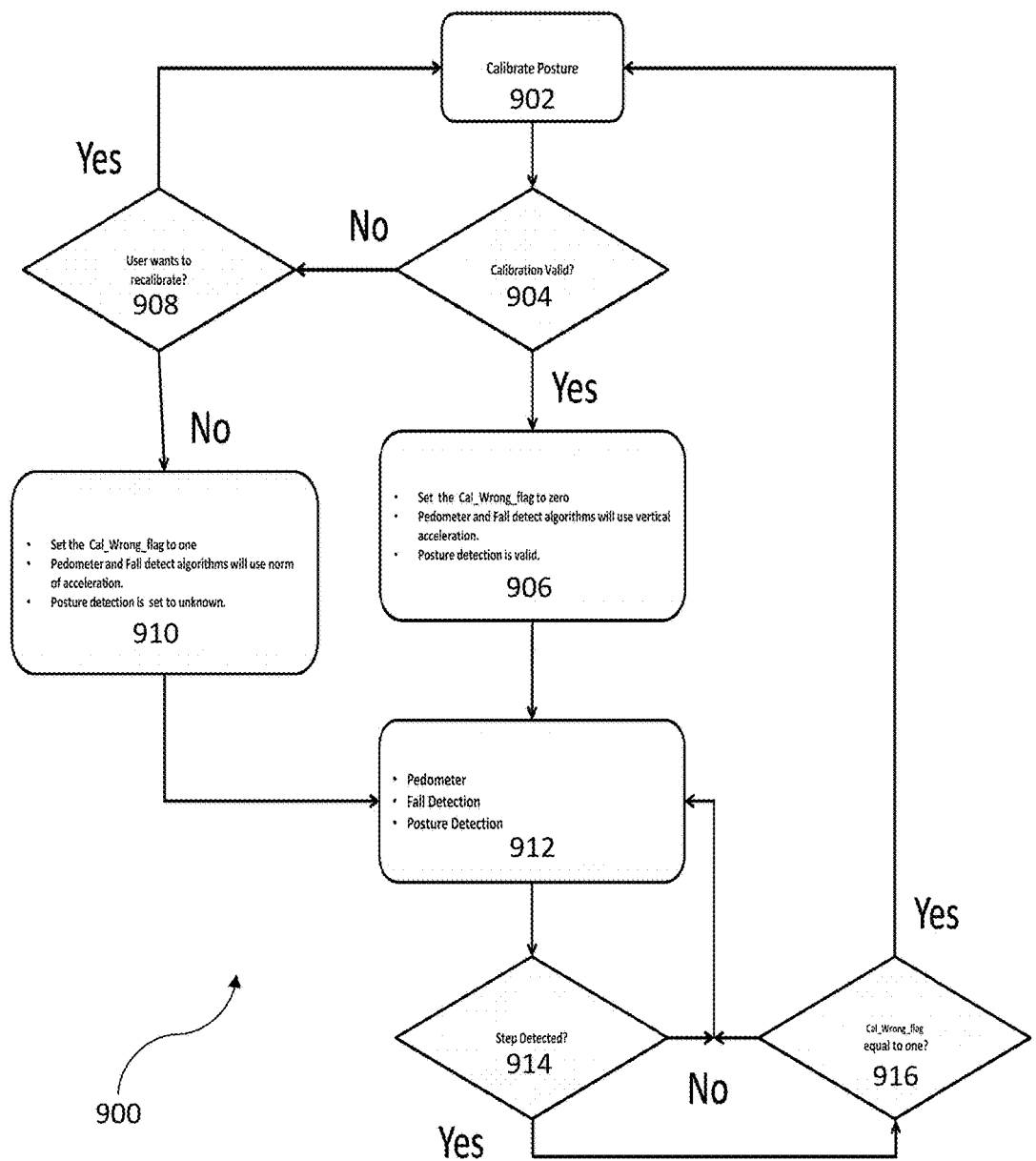
FIG. 9 illustrates a method for calibration validation in accordance with an embodiment.

Additional Calibration Techniques:

FIG. 9 illustrates a method 900 for calibration validation in accordance with an embodiment. The wireless sensor device is attached to a user in any orientation and on any bodily location of the user. Referring to FIGS. 1 and 9 together, the method 900 comprises an explicit calibration of the user's posture to determine a calibration vector, via step 902. In one embodiment, calibrating the user's posture explicitly includes but is not limited to the user notifying the wireless sensor device 100 when the user is in a vertical position and the wireless sensor device 100 being attached to the user's chest when the user is in a vertical position.

In this embodiment, the user notifies the wireless sensor device 100 in a variety of ways including but not limited to tapping the wireless sensor device 100, selecting a button of the wireless sensor device 100, and interacting with a mobile application interface of the wireless sensor device 100. Furthermore, in this embodiment, when the wireless sensor device 100 is attached to the user's chest while the user is in a vertical position, the wireless sensor device 100 recognizes contact impedance to confirm attachment between the user and the wireless sensor device 100.

The wireless sensor device 100 checks to see whether the explicitly determined calibration vector is valid, via step 904. If the determined calibration vector is valid, the wireless sensor device 100 sets cal_wrong_flag to zero (0), uses a vertical acceleration based on the validated calibration vector in both pedometer activity and fall detection algorithms, and confirms posture detection is valid, via step 906.

In FIG. 9, if the explicitly determined calibration vector is not valid, the wireless sensor device 100 displays a validation failure message to the user prompting the user to determine whether the user wants to explicitly recalibrate another calibration vector, via step 908. If the user wants to explicitly recalibrate another calibration vector, the method 900 returns back to step 902. If the user does not want to explicitly recalibrate another calibration vector, the method 900 sets cal_wrong_flag to one (1), uses a norm of acceleration in both pedometer activity and fall detection algorithms, and sets posture detection to unknown, via step 910.

In this embodiment, when the determined calibration vector is not valid, the wireless sensor device 100 monitors the activity of the user using a set of algorithms that are independent of the calibration vector.

In one embodiment, the determined calibration vector is checked for validity by ensuring a magnitude of acceleration along an anteroposterior axis of the user is less than a predetermined threshold including but not limited to g*sin(π/6), where g is the acceleration due to gravity. In this embodiment, if the magnitude of acceleration along the anteroposterior axis of the user is less than the predetermined threshold, then the calibration vector is determined to be valid and the method 900 proceeds to step 906. However, if the magnitude of acceleration along the anteroposterior axis of the user is greater than or equal to the predetermined threshold, then the calibration vector is determined to be invalid and the method 900 proceeds to step 908. The anteroposterior axis of the user measures the axis from the front chest to the back of the user and is nearly perpendicular to gravity when the user is in a vertical posture.

Figure 10:
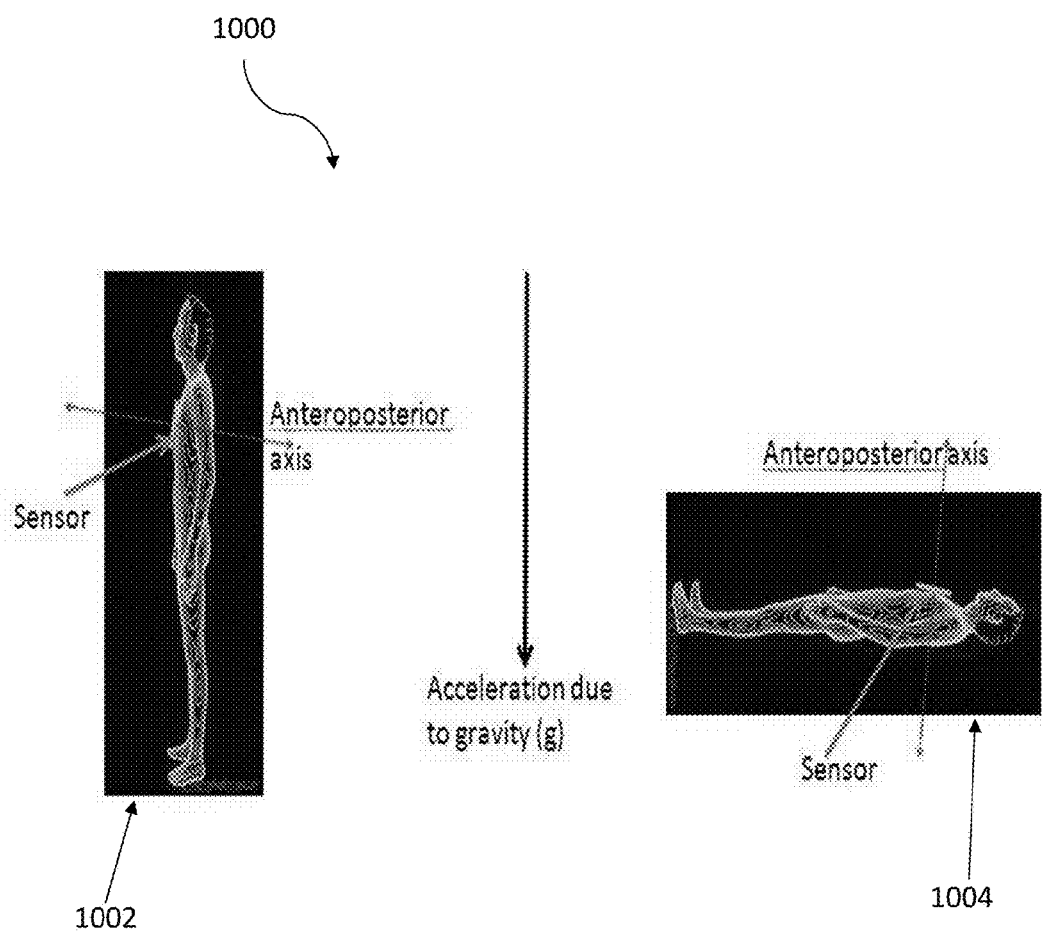
FIG. 10 illustrates a diagram of calibration vector checking in accordance with an embodiment.

FIG. 10 illustrates a diagram 1000 of calibration vector checking in accordance with an embodiment. The diagram 1000 includes a first scenario 1002 where the calibration check passes because an absolute value of acceleration along the anteroposterior axis of the user is less than the predetermined threshold. The diagram 1000 includes a second scenario 1004 where the calibration check fails because an absolute value of acceleration along the anteroposterior axis of the user is greater than or equal to the predetermined threshold.

Referring back to FIG. 9, after both steps 910 and 906, the user's activity including but not limited to pedometer activity, fall detection, and posture detection is monitored using various algorithms depending upon whether the calibration vector is validated or not, via step 912. In one embodiment, monitoring the activity of the user using the validated calibration vector includes but is not limited to monitoring pedometer activity using a vertical component of an acceleration vector of the user, monitoring fall detection using p-norm of the acceleration vector to detect an impact and an angle of the acceleration vector with respect to the validated calibration vector thereby determining a horizontal position of the user after impact, and monitoring posture detection using both the acceleration vector and the validated calibration vector.

In another embodiment, monitoring the activity of the user using a non-validated calibration vector due to a validation failure includes but is not limited to monitoring pedometer activity using 2-norm of an acceleration vector of the user and monitoring fall detection using p-norm of the acceleration vector to detect an impact. In this embodiment, the monitoring of fall detection does not calculate an angle and the posture of the user is unknown. Accordingly, it is desirable to monitor the activity of the user using a validated calibration vector.

Therefore, the activity algorithms utilized by the wireless sensor device 100 vary when using a validated calibration vector and when not using a validated calibration vector. In one embodiment, current acceleration (a) and calibration vectors (c) are utilized by the wireless sensor device 100 in the activity algorithms with a=(ax, ay, az) and c=(cx, cy, cz) when the calibration vector is validated.

In this embodiment, the activity algorithms that include a validated calibration vector comprise a pedometer activity algorithm that is based on a vertical component of the acceleration vector (pedometer activity (v)=a·c=ax*cx+ay*cy+az*cz), a fall detection algorithm that is based on p-norm of a to detect an impact and angle of a with respect to c to determine a horizontal position of the user after impact (p-norm of a=(|ax|^p+|ay|^p+|az|^p)^(1/p), for p>=1; angle of a calculated using a·c and 2-norms of a and c), and a posture detection algorithm that is based on a·c, cz and az.

Furthermore, in another embodiment, the activity algorithms that are utilized by the wireless sensor device 100 when not using a validated calibration vector include but are not limited to a pedometer activity algorithm that is based on 2-norms of a, a fall detection algorithm that is based on p-norm of a to detect an impact where no angle of a is calculated, and no posture detection algorithm because the posture of the user is unknown.

In the method 900, once footsteps of the user are detected by a pedometer type device that has been integrated into the wireless sensor device 100, via step 914, the wireless sensor device 100 utilizes implicit calibration to determine a new calibration vector. In one embodiment, the implicit calibration includes but is not limited to the wireless sensor device 100 deriving a vertical position based on an acceleration vector corresponding to footsteps when the user is walking. After the implicit calibration, the method 900 checks to see whether cal_wrong_flag is equal to one (1), via step 916.

If cal_wrong_flag is equal to one (1) indicating that the wireless sensor device 100 has been monitoring the activity of the user using a non-validated calibration vector, the method 900 returns back to step 902 to validate the new calibration vector. If cal_wrong_flag is not equal to one (1), indicating that the wireless sensor device 100 has been monitoring the activity of the user using a validated calibration vector, the method 900 returns back to step 912 and the wireless sensor device 100 continues the activity monitoring of the user.

Figure 11:
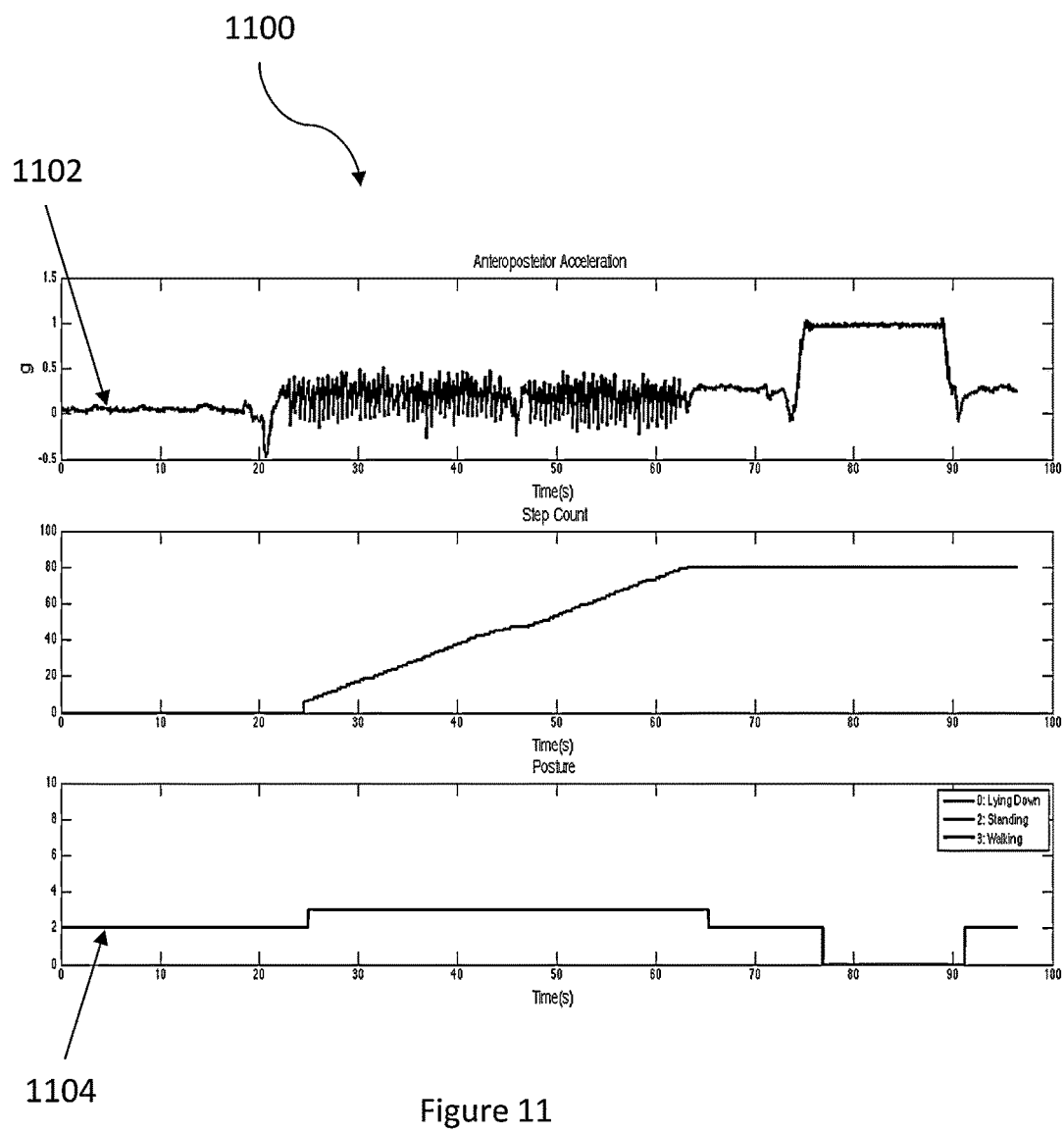
FIG. 11 illustrates a diagram of an example of explicit calibration in accordance with an embodiment.

FIG. 11 illustrates a diagram 1100 of an example of explicit calibration in accordance with an embodiment. The diagram 1100 plots anteroposterior acceleration, step count, and posture of the user over a predetermined time period. The diagram 1100 starts with a valid explicit calibration 1102 corresponding to a known standing posture 1104 of the user. The explicit calibration is valid because the user is in a standing posture when the user has notified the wireless sensor device to explicitly calibrate or the wireless sensor device has been attached to the user while in a standing posture.

As the step count of the user increases, the anteroposterior acceleration fluctuates and the posture of the user is identified to be in a walking posture. At approximately sixty (60) seconds, the step count of the user doesn't increase anymore thereby illustrating another change in the user's posture.

Figure 12:
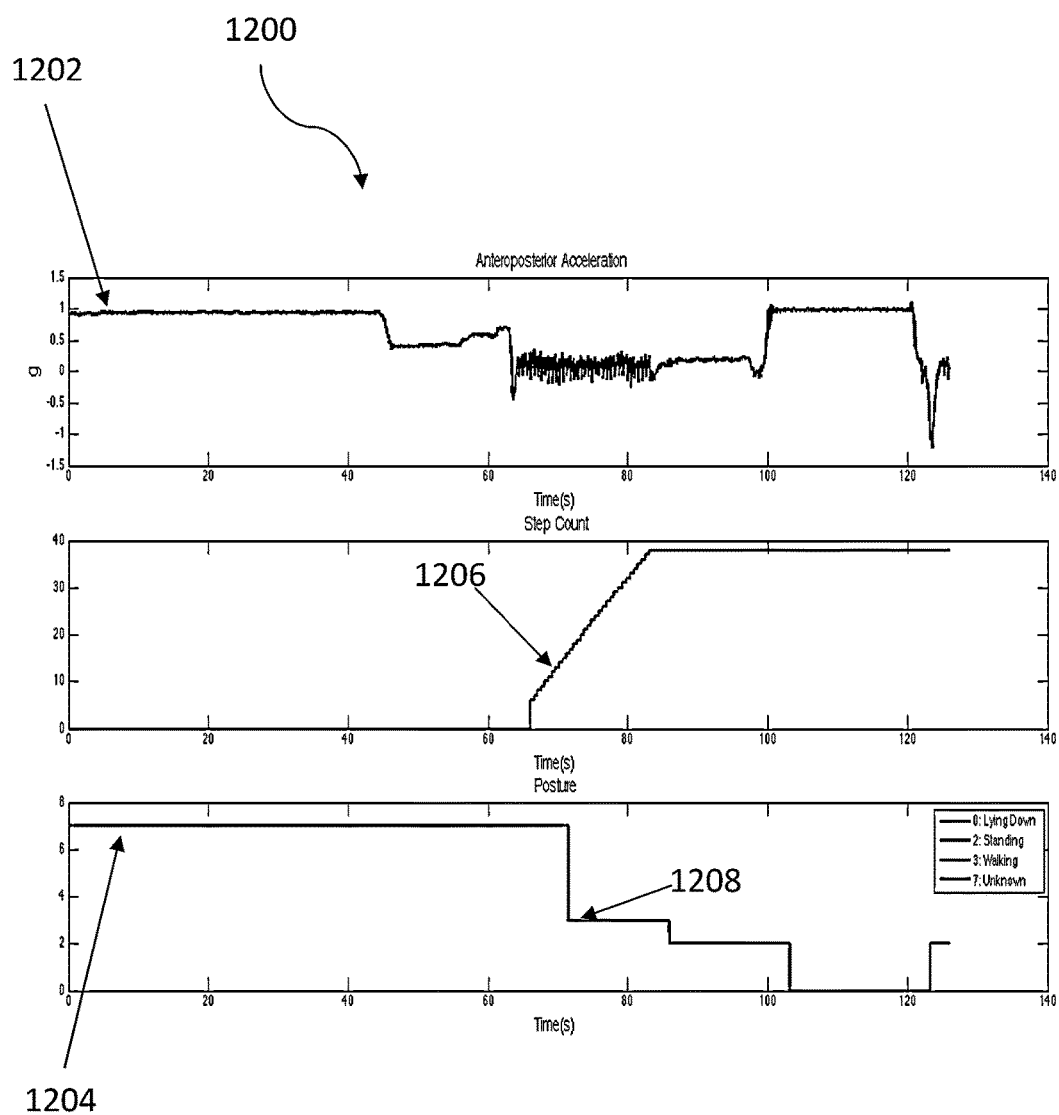
FIG. 12 illustrates a diagram of an example of implicit calibration in accordance with an embodiment.

FIG. 12 illustrates a diagram 1200 of an example of implicit calibration in accordance with an embodiment. The diagram 1200 plots anteroposterior acceleration, step count, and posture of the user over a predetermined time period. The diagram 1200 starts with an invalid explicit calibration 1202 corresponding to an unknown posture 1204 of the user. The explicit calibration is invalid because the user is in an unknown posture when the user has notified the wireless sensor device to explicitly calibrate or the wireless sensor device has not been attached to the user while in a standing posture.

As aforementioned, due to this invalid explicit calibration, the wireless sensor device attached to the user will monitor the user's activity by utilizing activity algorithms that do not incorporate a calibration vector. As the step count of the user increases, implicit calibration while walking 1206 occurs to incorporate a newly determined calibration vector into the activity algorithms utilized by the wireless sensor device. At this time while the user is walking, which is at approximately seventy (70) seconds, the wireless sensor device calculates a known posture of the user 1208.

As above described, the method and system allow for calibration of a chest-mounted wireless sensor device for posture and activity detection of a user. By implementing at least an accelerometer within a wireless sensor device to detect acceleration and posture samples and an application located on the wireless sensor device to process the detected acceleration and posture samples, and calibrating the wireless sensor device using a variety of automatic and manual calibration methodologies, an efficient and cost-effective calibration system is achieved that can support various types of activities and can confirm changes in a user's posture.

A method and system for calibration of a chest-mounted wireless sensor device for posture and activity detection of a user have been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application provides instructions that enable the processor to perform the functions described herein.

Furthermore, embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk. Current examples of optical disks include DVD, compact disk-read-only memory (CD-ROM), and compact disk-read/write (CD-RAN).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for calibrating a wireless sensor device, the method comprising:
   detecting accelerometer data in 3 axes within a predetermined time period by the wireless sensor device;
   determining an acceleration vector corresponding to a footstep number;
   determining a vertical calibration vector using the acceleration vector and a walking detection algorithm, wherein the walking detection algorithm:

calculates a signal magnitude area (SMA) for the predetermined time period using the accelerometer data, calculates a magnitude of acceleration in a horizontal plane and an overall magnitude of acceleration, and compares the SMA to a first threshold and the overall magnitude of acceleration to both a second threshold and a third threshold for a result of the walking detection algorithm; and determining a rotation matrix using the determined vertical calibration vector to line up native axes of the wireless sensor device with body axes.

2. The method of claim 1, wherein the determining the vertical calibration vector, when executed by a processor via the application, further comprises:

determining the vertical calibration vector using at least one of: automatic calibration, adaptive calibration, or manual calibration.

3. The method of claim 2, wherein the determining the vertical calibration vector using the automatic calibration comprises:

determining the acceleration vector corresponding to the footstep number of a user of the wireless sensor device; and determining whether the footstep number meets a minimum footstep number threshold within the predetermined time period.

4. The method of claim 2, wherein the determining the vertical calibration vector using the adaptive calibration comprises:

detecting an inaccuracy with the automatic calibration; and adjusting the vertical calibration vector slowly over time.

5. The method of claim 4, wherein the adjusting the vertical calibration vector slowly over time comprises:

adding current acceleration samples during a detected walking period; and normalizing the vertical calibration vector to provide an adjusted calibration vector.

6. The method of claim 2, wherein the determining the vertical calibration vector using the manual calibration, when executed by the processor via the application, comprises:

determining the vertical calibration vector using at least one of: upright manual calibration, manual calibration based on walking, or bedridden manual calibration.

7. The method of claim 6, wherein the determining the vertical calibration vector using the upright manual calibration comprises:

receiving an upright manual calibration request from a user in a standing upright position via a relay;

detecting a MEMS based vertical calibration vector;

filtering the MEMS based vertical calibration vector using a lowpass filter;

replacing a current upright vertical calibration vector with the filtered MEMS based vertical calibration vector; and transmitting a status message to the relay.

8. The method of claim 6, wherein the determining the vertical calibration vector using the manual calibration based on walking comprises:

receiving a manual calibration request from a user during a walking period via a relay;

calculating a MEMS based vertical calibration vector during the walking period;

determining whether the walking period meets another minimum footstep number threshold; and transmitting a status message to the relay.

9. The method of claim 6, wherein the determining the vertical calibration vector using the bedridden manual calibration comprises:

receiving a manual calibration request from a bedridden user via a relay;

determining both a supine calibration vector and a leaning calibration vector;

calculating a MEMS based vertical calibration vector based on the supine calibration vector and the leaning calibration vector; and transmitting a status message to the relay.

10. The method of claim 6, wherein the manual calibration based on walking, when executed by the processor via the application, further causes the processor to:

receive a manual calibration request from a user during a walking period via a relay;

calculate a MEMS based vertical calibration vector during the walking period;

determine whether the walking period meets another minimum footstep number threshold; and transmit a status message to the relay.

11. A wireless sensor device, comprising:

a processor; and a memory device coupled to the processor, wherein the memory device includes an application that, when executed by the processor, causes the processor to:

detect accelerometer data in 3 axes within a predetermined time period by the wireless sensor device;

determine an acceleration vector corresponding to a footstep number;

determine a vertical calibration vector using the acceleration vector and a walking detection algorithm, wherein the walking detection algorithm:

calculates a signal magnitude area (SMA) for the predetermined time period using the accelerometer data, calculates a magnitude of acceleration in a horizontal plane and an overall magnitude of acceleration, and compares the SMA to a first threshold and the overall magnitude of acceleration to both a second threshold and a third threshold for a result of the walking detection algorithm; and determine a rotation matrix using the determined vertical calibration vector to line up native axes of the wireless sensor device with body axes.

12. The device of claim 11, wherein the determine the vertical calibration vector comprises:

determine the vertical calibration vector using at least one of: automatic calibration, adaptive calibration, or manual calibration.

13. The device of claim 12, wherein the determine the vertical calibration vector using the automatic calibration comprises:

determine the acceleration vector corresponding to the footstep number of a user of the wireless sensor device; and determine whether the footstep number meets a minimum footstep number threshold within the predetermined time period.

14. The device of claim 12, wherein the determine the vertical calibration vector using the adaptive calibration comprises:

detect an inaccuracy with the automatic calibration; and adjust the vertical calibration vector slowly over time.

15. The device of claim 14, wherein the adjust the vertical calibration vector slowly over time comprises:
- add current acceleration samples during a detected walking period; and
- normalize the vertical calibration vector to provide an adjusted calibration vector.

16. The device of claim 12, wherein the determine the vertical calibration vector using the manual calibration comprises:
- determine the vertical calibration vector using at least one of: upright manual calibration, manual calibration based on walking, or bedridden manual calibration.

17. The device of claim 16, wherein the upright manual calibration, when executed by the processor via the application, further causes the processor to:
- receive an upright manual calibration request from a user in a standing upright position via a relay;
- detect a MEMS based vertical calibration vector;
- filter the MEMS based vertical calibration vector using a lowpass filter;
- replace a current upright vertical calibration vector with the filtered MEMS based vertical calibration vector; and
- transmit a status message to the relay.

18. The device of claim 16, wherein the bedridden manual calibration, when executed by the processor via the application, further causes the processor to:
- receive a manual calibration request from a bedridden user via a relay;
- determine both a supine calibration vector and a leaning calibration vector;
- calculate a MEMS based vertical calibration vector based on the supine calibration vector and the leaning calibration vector; and
- transmit a status message to the relay.

* * * * *